United States Patent [19]

Kamarei et al.

[11] Patent Number: 4,957,741

[45] Date of Patent: Sep. 18, 1990

[54] METHOD FOR THE TREATMENT OF GASTRIC ULCER

[75] Inventors: Ahmad R. Kamarei, Lexington; Nicholas Catsimpoolas, Newton Center; Robert McCluer, Acton, all of Mass.; Takashi Mise, Yokohama, Japan; Robert S. Sinn, New York, N.Y.

[73] Assignee: Angio-Medical Corp., New York, N.Y.

[21] Appl. No.: 227,533

[22] Filed: Aug. 2, 1988

[51] Int. Cl.$^5$ .................... A61K 35/30; A61K 35/12; A61K 31/70
[52] U.S. Cl. ...................................... 424/551; 514/25; 514/925; 514/926; 514/927; 424/570
[58] Field of Search .................... 424/95; 514/25, 925, 514/926, 927

[56] References Cited

U.S. PATENT DOCUMENTS 4,710,490 12/1987 Catsimpoolas et al. .............. 514/25

FOREIGN PATENT DOCUMENTS 0146810 7/1985 European Pat. Off. ............ 514/926
1057594 3/1986 Japan .................................. 514/925

OTHER PUBLICATIONS

Okuyama, E., et al., The Principles of Tetragonia tetragonoides having Anti-Ulcerogenic Activity. II. Isolation and Structure of Cerebrosides, Chemical Pharmaceutical Bulletin, vol. 31, pp. 2209–2219.

*Primary Examiner*—Jacqueline Stone
*Assistant Examiner*—Jean Witz
*Attorney, Agent, or Firm*—Felfe & Lynch

[57] ABSTRACT

Lipid material or ganglioside from mammalian sources e.g. bovine and porcine brain or omentum is used to treat peptic ulcers.

3 Claims, 3 Drawing Sheets

METHOD FOR THE TREATMENT OF GASTRIC ULCER

SUMMARY

The invention concerns treatment of stomach and duodenal ulcers with either omental extracts or ganglioside materials.

DESCRIPTION

Figure 1:
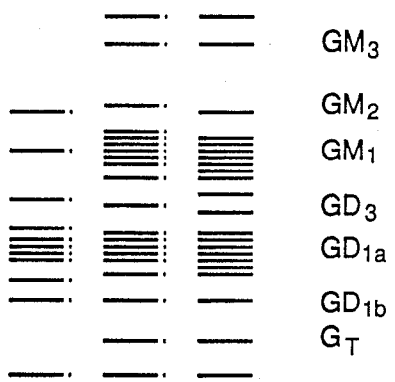
FIG. 1 shows a thin layer chromatograph (TLC) of bovine brain ganglioside (BBG) preparations.
Figure 2:
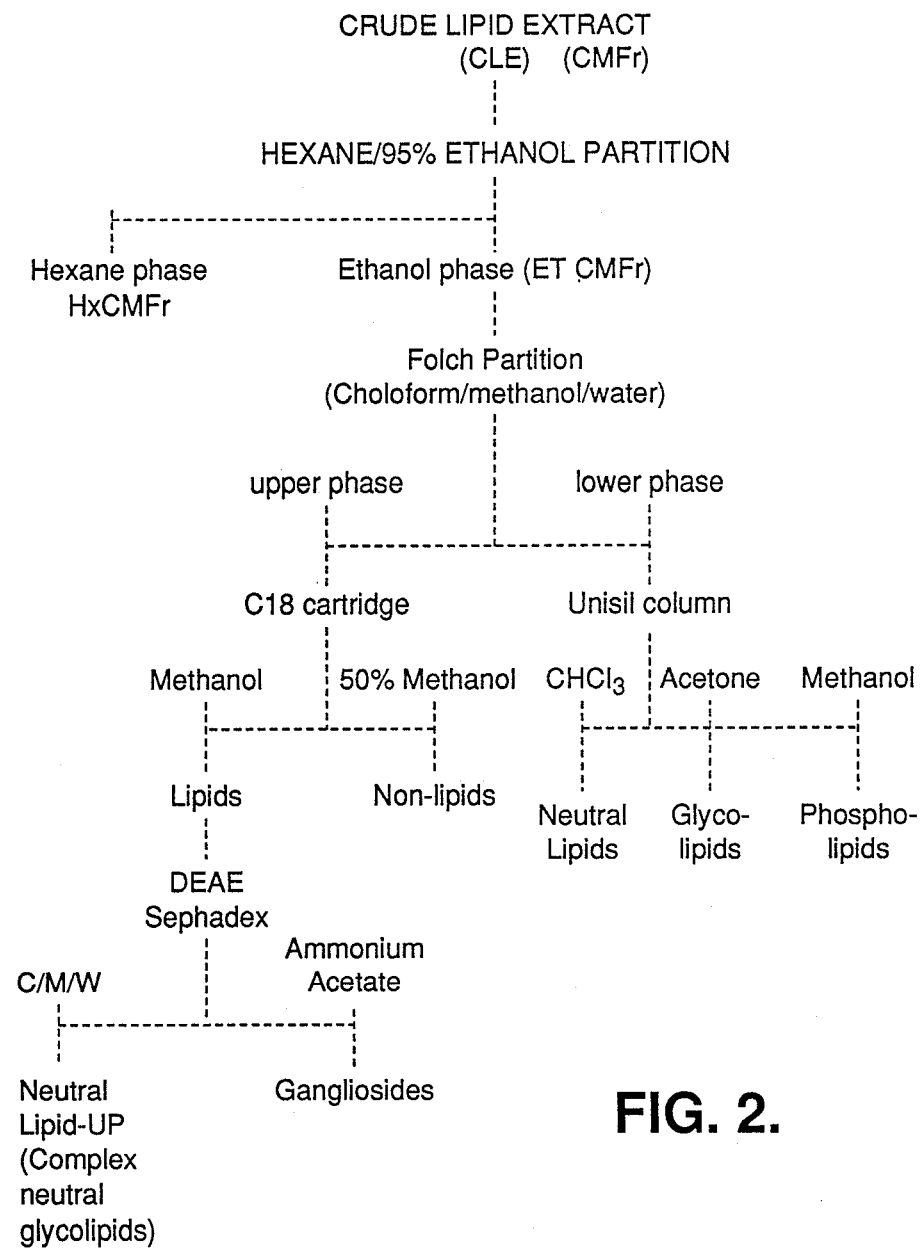
FIG. 2 shows fractionation of mammalian lipid omental material extracted by chloroform:methanol 2:1 to show the various components any of which separately or together may contribute to the antiulcer effect.
Figure 3:
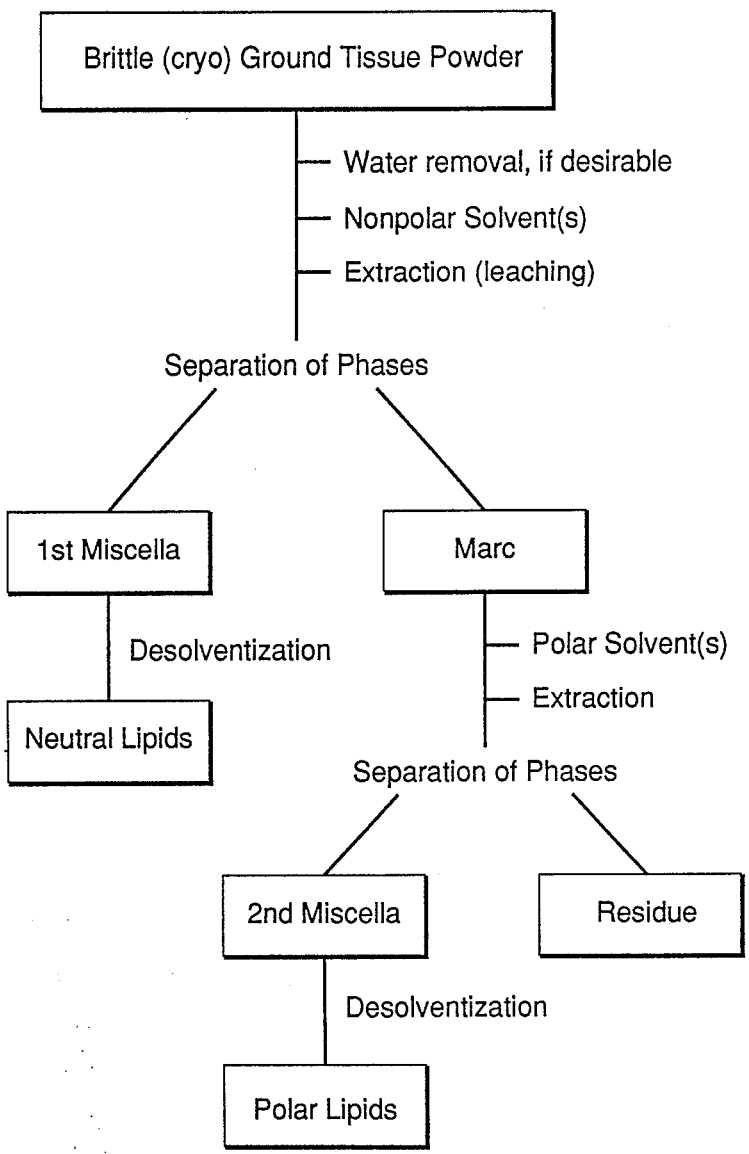
FIG. 3 shows hexane-ethanol sequential extraction of porcine omentum.

Peptic ulcers, which includes duodenal, gastric, channel postbulbar, marginal or stomal ulcers, jejeunal or stress ulcers have been treated for a long time by pharmaceutical agents. Subsequent surgical removal of all or part of the stomach or intestine occurs commonly when pharmaceutical methods have failed or penetration, perforation, malignancy or hemorrhage occur. Current favored drugs for ulcer treatment are histamine $H_2$ receptor blocking agents such as cimetidine. Cimetidine competitively inhibits histamine binding at $H_2$ receptors, thus blocking gastric acid secretion, stimulated by histamine, gastric parasympathetic activity and food. It decreases both basal and nocturnal gastric acid secretion, and reduces pepsin, intrinsic factor, secretion and gastric juice volume. In general, $H_2$ antagonists have an imidazole ring with some longer, more complex sidechain than the ethylenediamine side chain of histamine.

Other pharmacological agents which have been used in the treatment of peptic ulcers include sucralfate, a sucrose and aluminum containing disaccharide, and sulpiride, reported to act on the hypothalmus to diminish gastric secretion. Bismuth compounds such as Zolimidine and colloidal bismuth subcitrate and perhaps Peptobismol TM are described and in use in Britain and Scandinavia. U.S. Pat. No. 4,153,685 issued May 8, 1979 to Serfonteen describes protein complexes with bismuth. Carbenoxolone has also been used to effect healing of gastric and duodenal ulcers but its side effects detract from its usefulness; and it is not used in the U.S.

Certain prostaglandins ($PGE_1$, $PGE_2$, PGA) and their 16,16-dimethyl analogs inhibit gastric HC1 secretion stimulated by histamine, pentagastrin or food. However advantages over existing drugs have yet to be demonstrated.

Applicants note U.S. Pat. No. 3,932,463 issued Jan. 13, 1976 to Schaub et al. concerning 11-dioxy-13-dihydro-prostaglandin-9-ketals and U.S. Pat. No. 4,017,534 issued Apr. 12, 1977 to Schaub et al. concerning 16-fluoro-11-deoxy-13-dihydroprostaglandin wherein both patents show use of the compounds as gastric acid secretion inhibitors. Prostaglandin analogues of $PGE_1$, $PGE_2$, $PGA_1$ and $PGA_2$ are disclosed in U.S. Pat. No. 3,903,297 issued Sept. 2, 1975 to Andre Robert for prophylaxis and treatment of gastric hypersecretion, gastric and duodenal ulcers.

Applicants also note U.S. Pat. No. 4,530,837 issued July 23, 1985 to Charon which discloses peptide derivatives as antagonists of gastrin and histamine. U.S. Pat. No. 4,428,942 issued Jan. 31, 1984 discloses analogues of the tetradecapeptide somatostatin which inhibit secretion of gastrin; however the analogues appear to be inactive against gastrin secretion.

In Ann. Surg. 201:290 (1985) Sakamoto, T., et al. study stress induced ulcers and show a lower ulcer index for pentagastrin combined with EGF (epidermal growth factor), which may be accounted for by the endogenous somatostatin content of their material.

U.S. Pat. No. 4,370,317 issued Jan. 25, 1983 to Jorgensen et al. discloses a polypeptide which may be useful for treatment of gastroduodenal ulcers by inhibition of pentagastrin stimulated gastric acid secretion.

According to this patent the frequently demonstrated side reactions of cimetidine include diarrhea, exanthema, elevation of liver enzymes and gynecomastia. Further, there is some disclosure relating to use of glycoside-hydrolase inhibitors of microbial origin.

Klagsbrun, M. and Shing, Y..W. in *Pediatr Res.* 19:916 (1985) obtained a growth factor similar to EGF from human milk that appeared to reduce the incidence, number and severity of cysteamine-induced duodenal ulcers. This positive effect of EGF-type material is echoed in the article by Shove-Olsen, P. et al. in *Gastroenterology* 90:911 (1986) using synthetic human EGF-/urogastrone which healed chronic duodenal ulcers as well as cimetidine.

However the history shows no use of lipid materials, particularly but not exclusively omental material or ganglioside material for healing of ulcers. The present work shows this healing effect in mammals. The following examples are described in order to be illustrative but not limitative of the present invention and it is understood that other embodiments within the spirit and scope of the invention will suggest themselves to those skilled in the art.

The extraction of omental material wherein CMFr is the chloroform-methanol fraction is described in the U.S. Pat. No. 4,699,788 issued Oct. 3, 1987. Further methodology is included in the U.S. Pat. Application Ser. No. 4,710,490 issued Dec. 1, 1987 and U.S. Pat. Application Ser. No. 852,444 now allowed. All the above are hereby incorporated by reference.

Methods for isolation of ganglioside mixtures and description herein below (also see Table 1. FIG. 1).

Essentially, however, the many methods for obtaining gangliosides from animal tissue involve three main steps of varying complexity, extraction, isolation and purification. The most common and benchmark procedure is Folch partitioning of the total lipid extract (chloroform/methanol/water). Gangliosides partition into the upper methanol/water phase, and most of the neutral lipids into the lower phase. Folch-Pi, J., Lees, M., Sloane-Stanley, G.H., J. Biol. Chem. 226:497–509 (1957); Trams, E. and C.J. Lauter; *Biochemica et Biophysica Acta*, 60:350, (1962); Autilio, L.A. and W. T. Norton, *Journal of Neurochemistry*, 12:543 (1965), Tettamanti, G., et al. *Biochemica et Biophysica Acta., Vol.* 296:160 (1973), Quarles, R. and J. Folch-Pi, *Journal of Neurochemistry*, 12:543 (1965), Svennerholm, L. and P. Fredman, *Biochemica et Biophysica Acta.*, 617:97 (1980); Nilsson, O. and L. Svennerholm, *Journal of Lipid Research*, 23:327 (1982).

Isolation and purification of gangliosides from the upper phase can proceed according to methods known in the art. Isolation and purification of gangliosides usually requires long, complex procedures and is performed for analytical purposes or on small quantities of starting tissue or lipid material because of the large volumes of organic solvent required.

Ganglioside isolation and purification may require other steps, including removal of other contaminating lipids, dialysis, chemical precipitation or chromatography on:

(1) Silica gel: Gray, G., *Biochemica et Biophysica Acta*, 144:511 (1967); McCluer, R.H. and J.E. Evans, *Journal of Lipid Research*, 14:611 (1973); Ando, S., et al., *Biochemica et Biophysica Acta.*, 424:98 (1976); Kawamura, N. and T. Taketomi, *J. biochemistry*, 81:1217 (1977); Irwin, C.C. and L.N. Irwin, *Analytical Biochemistry*, 94:335 (1979); Leskawa, K.E. et al., *Analytical Biochemistry*, 140:172 (1984);

(2) Reverse phase packings: Yamazaki, J., et al., *J. Biochemistry*, 86:803 (1979); Gross, S.K. and R.H. McCluer, *Analytical Biochemistry*, 102:429 (1980); Sonnino, S., et al. *J. of Lipid Research*, 25:620 (1984); Watanabe, K. and Y. Tomono, *Analytical Biochemistry*, 139:367 (1984); Sonnino. G., et al., *J. of Neuroscience Research*, 12:179 (1984);

(3) Ion-exchange packings: Ledeen, R.W. and R.K. Yu, *J. of Lipid Research*, 13:680 (1972); Momoi, T., et al., *Biochemica et Biophysica Acta.*, 441:488 (1976); Iwamosi, M. and Y. Nagai, *Biochemica et Biophysica Acta*, 528:257 (1978); Fredman, P., et al., *Biochemica et Biophysica Acta.*, 618:42 (1980); Suzuki, Y., et al., *Lipids*, 20; No. 9:588 (1985); Mansson, J.E., et al., *J. of Chromatography.*, 322:465 (1985); Smid, F., et al., *J. of Chromatography*, 377:69 (1986); Whalen, M., et al. *Lipids*, 21: No. 4 (1986);

(4) thin-layer: Eberlein, K. and G. Gercken, *J. of Chromatography*, 16:425 (1975); Ando. S., et al., *Analytical Biochemistry*, 89:437 (1978); Harth, S., et al., *Analytical Biochemistry*, 86:543 (1978); Randell, J.A. and C.A. Pennock, *J. of chromatography*, 195:257 (1980); Hunter, G.D., et al., *J. of Neurochemistry*, 37 (4):1025 (1981); Sonnino, S. et al., *Analytical Biochemistry*, 128:104 (1983).

EXAMPLE 1

Ganglioside extraction and isolation

Usually, cryoground tissue is extracted with chloroform/ methanol (2:1, 1:1 or 1:2) in a blender and tissue residue removed by filtration. Aqueous salt solution (0.2 total volume) is added to the extract to effect phase separation. The lower-phase is back washed repeatedly with theoretical upper phase (TUP methanol-water) to increase ganglioside recovery and all the aqueous upper-phases are combined and desalted on a C-18 reverse phase packed column. The column eluate is dried, resuspended and subjected to alkaline- hydrolysis to destroy ester bonds of unwanted neutral and phospholipids. After desalting on C18, the material is applied to DEAE-Sephadex to separate neutral and acidic glycosphingolipids (gangliosides). The eluate containing gangliosides is again desalted on C-18, to remove ammonium salts and the gangliosides eluted with methanol again brought to dryness and finally taken up in chloroform methanol.

EXAMPLE 2

Bovine Brain Ganglioside Isolation Procedure
Materials

All solvents were reagent grade and were obtained from Fisher Scientific (Fairlawn, N.J.). Reverse phase C18 preparative packing was obtained from Analytichem (Harbor City, Calif.); Merck HPTLC plates were purchased from Curtin Matheson (Houston, Tex.); DEAE Sephadex A-25 was obtained from Pharmacia (Piscataway, N.J.).

Method 1

1 kg cryoground bovine brain was extracted with 15 volumes (10 volumes and then 5 volumes) Chloroform: Methanol (2:1) at room temperature. (See U.S. Pat. No. 4,776,173 thereby incorporated by reference). The mixture was centrifuged at 2000 RPM for 10 minutes at 25° C. After centrifugation there was a distinct separation consisting of solid upper phase (tissue residue) and the lower organic phase, which was collected and vacuum-filtered with Whatman #4 & #54.

All extracts were combined and the solvent was rotary-evaporated at 37° C. 147.3 g of yellow lipid material having no distinct odor was collected. The above lipid was redissolved in 30 volumes of C:M (2:1) and partitioned with 1/5 volumes of distilled $H_2O$ (882 mls) and centrifuged at 2000 RPM; 10 minutes; 25° C.

The upper phase and interface were collected by vacuum and the remaining phases were allowed to separate in a separatory funnel.

The lower phase was twice washed with theoretical upper phase or TUP (3:48:47), 2000mls and 2010 mls. Each washing was thoroughly mixed by rotation on evaporator flask, then centrifuged twice at 2000 RPM, 15 minutes; 25° C.

The following phases were collected:

Total Upper Phase collected 6270 mls (−100 ml inv)=6170 mls

Total Lower Phase collected 2510 mls (−100 ml inv)=2410 mls

Total Interface collected 97.7 g(−10.0 g inv)=87.7 g

Total Residue collected 538.0 g (−25.0 g inv)=513.0 g

The upper phase was then used for the final steps of ganglioside extraction.

Method 2

Adult beef brain, approximately 1 kg was cryoground and the lipids were extracted according to the method of Folch et al. (Folch, J.; Lees, M. and Sloan Stanley, G.H., supra). Briefly, the tissue was extracted with 20 volumes of chloroform:methanol (2:1, v/v) and the extract was filtered to remove the residue. The resulting lipid extract was then partitioned by the addition of 0.2 volumes of water, mixed thoroughly and allowed to separate into two phases. The upper phase was removed and the lower phase was washed one time with an equal volume of theoretical upper phase ($CHCl_3$:MeOH:$H_2O$; 3:47:48 v/v/v). The two upper phases were combined.

The upper phase was brought to a final concentration of 0.1 M KCl and applied to a reverse phase C18 column according to the method of Williams and McCluer (Williams, M.A., et al. (1980) J. Neurochem. 35:226–269). After desalting the gangliosides were eluted from the column using C:M (1:1). The sample was taken to dryness and treated with 0.5 M methanolic-NaOH at, 37° C. for 2.0 hours to destroy ester lipids. The mixture was then neutralized with acetic acid and desalted again using the C18 column described above. The C:M (1:1) fraction containing neutral and acidic glycosphingolipids was taken to dryness.

Neutral glycosphingolipids and gangliosides were separated using ion exchange chromatography. The mixture was dissolved in methanol and applied to a DEAE-Sephadex column (25 ml of swelled resin) as described by Ledeen and Yu (Ledeen, R.W. (1982) Methods of Enzymol. 83:139-191). Neutral glycolipids were eluted using five volumes (125 ml) of methanol. The total ganglioside mixture was eluted from the anion exchange resin with 10 volumes (250 ml) of 0.5 M ammonium acetate in methanol. The ganglioside fraction was taken to dryness and again desalted as described above.

This fraction was redissolved in methanol and an aliquot applied to a Merck HPTLC plate and developed using chloroform/methanol/0.25% $CaCl_2$ (55:45:10). The gangliosides were visualized with resorcinol reagent. The major components of this mixture are GD1a, GT1b, GM1 and GD1b.

Finally, the gangliosides were dissolved in water, lyophilized, and weighed. Approximately 440 mg were recovered from 1 kg bovine brain.

EXAMPLE 3

The preferred method for preparation of omentum for extractions is a brittle grinding (or cryogrinding) technique. Porcine omentum is preferred for use in the composition, however, bovine, feline, ovine or any other type of mammalian omentum may be used.

The omentum is cut or broken into pieces and frozen by a method described in U.S. Pat. No. 4,776,173 herein incorporated by reference.

An extremely fine, and free-flowing (non-sticky) cryoground tissue (tissue powder) results. In cryoground tissue powder, the ratio of surface area to volume increases tremendously, with a concomitant reduction of density. As an example, density of omentum powder is 0.44 ($\pm 5\%$) g/ml, about half the density of lipids extracted from omentum. If uniformity of the powder in a particular size range is desired for the following steps, tissue powder should be sieved at or below its brittleness temperature. For this purpose, one may use stacked stainless steel standard sieves having standard designations.

The uniform tissue powder can be further processed, transferred, or stored at regular freezing temperature (e.g., $-18°$ C.$=0°$ F.). However, even at regular freezing temperature some biochemical (enzymatic) as well as chemical changes may occur slowly, e.g., oxidation of unsaturated lipids, (especially because of tremendous surface area generated by cryogrinding), insolubilization or destabilization of proteins; and degradation of pigments and vitamins and other biomolecules. Reduction of freezer temperature will cause decline of the rates of the above reactions. Consequently, for longer storage times, it is recommended that the final tissue powder be stored at $-40°$ C., under vacuum or inert gas, and in the dark, (to prevent any possible photocatalytic reactions). Preliminary evaluation shows that various tissue powders stored at $-40°$ C. for up to 2 months, did not show any physical changes (texture, color, odor, etc.) in the product.

To use the uniform cryoground product, one should desirably thaw the tissue powder. Since thawing of non-fluid tissues is inherently slower than freezing, when comparable temperature differentials are employed (due to different thermal properties of ice vs. water), tissue powders may be subject to damage by chemical or physical (and less microbial or enzymatic) means. In light of these considerations, one skilled in the art will recognize that the thawing process must be carefully considered.

However, omentum powder (rather than more traditional cell breakage methods) facilitates processing and handling of the raw material for all types of follow-up extractions, and increases the percent lipid recovery.

PO CMFr Preparation (porcine omentum chloroform-methanol fraction)

Porcine omentum was cryoground and stored at $-40°$ C. Just before use, 1 Kg was thawed to room temperature and extracted with 10 vol. chloroform/methanol (2/1) at room temperature. The mixture was centrifuged at 2,000 rpm, 5 min., 25° C. to separate the residue from the extract; the extract was collected and dried under vacuum at 37° C. A whitish extract (911.1 g) of porcine omentum chloroform/methanol fraction (PO CMFr) was collected, a 91% recovery.

Omenta also were extracted from feline and bovine sources by this method and others as previously described, Goldsmith et al. (1984). Other lipid extraction methods can be used as well. The invention is not limited by the extraction method described above which is for illustrative purposes. Ovine and other omenta can also be extracted in the like manner.

Omentum may be extracted with other organic solvents, with detergents or with supercritical gases as described in our U.S. Pat. No. 4,673,667 issued June 16, 1987 and U.S. Pat No. 4,749,522 issued June 7, 1988, and hereby incorporated by reference.

A supercritical fluid has increased solvation power at temperatures above its critical pressure (Pc) and critical temperature ($T_c$). When $CO_2$ is used at 38-39° C. and 3500 psi, the extract contains the more non-polar materials including lipids such as triglycerides, and polar materials such as gangliosides mostly remain in the residue.

Lipids are displaced from complexes involving proteins, such as cell membranes or lipoproteins, by amphipathic detergents in aqueous media. The released lipid material is recovered by flotation after centrifugation as disclosed in U.S. Ser. No. 811,375 filed on Dec. 20, 1985, herein incorporated by reference.

We also note mild thermal extraction can be used to extract lipids from omentum or other fatty tissue.

Also see the paper by McCluer et al. Lipid 22:229 (No. 4) (1987) "Characterization of Feline Omental Lipids" hereby incorporated by reference.

EXAMPLE 4

Chloroform/Methanol Extraction of Omentum Powder 500 g. uniform cryoground porcine omentum powder was warmed up to room temperature and extracted with 10 volumes chloroform/methanol (2:1, v/v) in a glass blender (22,000 RPM, 30 seconds). The slurry was centrifuged (2,000 RPM, 20 minutes) separated from pellet and dried by rotary evaporation (under vacuum at 37° C.). A whitish chloroform/methanol fraction (CMFr) weighing 388 g. (i.e., 77.6%) was obtained.

EXAMPLE 5

Ulcer Test System

Male (200-250 g) Spraque-Dawley rats were subjected to clamping-cortisone treatment to produce the experimental gastric ulcers. Then the rats received intramuscular injections of porcine omentum chloroform/methanol extract (POCMFr), bovine brain gangliosides (BBG) or saline (control) for 28 days. Ten rats received each treatment in each experiment. On the day after the final treatment, the rats were sacrificed to examine the severity of the ulcer by gross observation and histopathological assessment.

The clamping-cortisone method produced gastric ulcers in 24 h fasted rats as follows:

The stomach of a rat fasted for the previous 24 h (day 0) was exposed by abdominal incision under ether anesthesia. A part of the greater curvature of stomach (at a position lower by 3 mm from the border of the clamped with a double-folded aluminum plate (12×4 mm). Following antisepsis the abdominal muscle and skin were sutured. The abdomen was opened again (day 2) to remove the clamping plate and gauze after 24 hours. The wall of the stomach was loosened carefully. The abdominal muscle and skin were sutured again. After the rats recovered from the second surgical intervention, they were allowed water and solid foods ad libitum (day 2). Hydrocortisone acetate (70 mg/kg) was injected intramuscularly once daily for 7 days from the day when the animals received the clamping plates (day 1).

On the day after the last hydrocortisone injection (day 8), animals in each treatment group of 10 received daily injections in the right or left femoralis muscle of POCMFr (0.1 ml/100 g body wt.), BBG (0.07 ml/100 g body wt. with 1 mg BBG/ml in phosphate-buffered saline) or phosphate buffered saline (control) (0.1 ml/100 g body wt).

The 10 rats in each group were sacrificed on day 36 after completing 28 days of treatment. The pylorus was ligated by the method of Brodie et al. (1960, Gastroenterology 38:353); about 12 ml of 0.5% formalin was poured through the lower end of the esophagus into the stomach and then the cardia was ligated, and the stomach was fixed in formalin for 10 min. Then, the ulcer was exposed by lesser curvative incision for gross observation, to determine the ulcer index, UI, as the length (a) times the width (b) (UI=a×b).

Parts of the stomach with ulcer were dissected, attached to filter papers, fixed in 10% formalin and stained with hematoxylin-eosin for histopathological evaluation and by Van Gieson's method for new collagen deposition. Data in Table (b 1 indicate some increased repair proceeds in BBG to POE treatment animals as compared control.

The means and standard errors of ulcer index for the three treatments are as follows:

|   |   | Ulcer Index (See TABLE 2) | | |
|---|---|---|---|---|
|   |   | Mean | SEM | N |
| 1. | Saline | 12.8 | 2.9 | 10 |
| 2. | CMFr | 5.9 | 2.5 | 9 |
| 3. | BBG | 0.3 | 0.3 | 10 |

The three treated groups are not from the same population (p=0.003) by Multiple Sample Tests - One Way ANOVA in the Hewlett-Packard Statistics Library Pairwise analysis by the unpaired Students' t test, gives p values (see also bottom of Table (b 2):

|   | POCMFr | BBG |
|---|---|---|
| Saline | .05 | .0002 |
| POCMFr |   | 0.02 |

Clearly, the groups treated with BBG and POCMfr are different from each other and from the saline treated group.

Animals treated with BBG received 0.07 mg/100 g body wt. of ganglioside daily. Animals treated with 0.1 ml POCMFr/100 g body received about 0.0054 mg/100 g body wt. of omental ganglioside daily, i.e. about 1/13 as much as bovine brain ganglioside. The difference in responses may be related to the amount or type of gangliosides in the two preparations.

TABLE 1

Treatment for 4 weeks with Bovine Brain Gangliosides (BBG) Porcine Omentum Chloroform-Methanol Fraction (POCMFr) or saline, of gastric ulcer induced by clamping-cortisone method in SD rats

| Histopathologic Findings | Treatment Dose (ml/kg) No. of animals Grade* | Saline 1 10 | | | | POCMFr 1 9 | | | | BBG 0.7 10 | | | |
|---|---|---|---|---|---|---|---|---|---|---|---|---|---|
| | | 0 | 1 | 2 | 3 | 0 | 1 | 2 | 3 | 0 | 1 | 2 | 3 |
| Necrosis, defect of mucous epithelium | | 7 | 1 | 2 | 0 | 6 | 2 | 0 | 1 | 8 | 1 | 1 | 0 |
| Cell infiltration | | 3 | 5 | 1 | 1 | 3 | 3 | 2 | 1 | 6 | 3 | 1 | 0 |
| Regeneration of mucous epithelium | | 0 | 2 | 7 | 1 | 0 | 2 | 5 | 2 | 0 | 6 | 3 | 1 |
| Increase of collagenous fibers | | 0 | 7 | 3 | 0 | 0 | 4 | 4 | 1 | 1 | 4 | 5 | 0 |
| Increase of fibroblast | | 6 | 2 | 2 | 0 | 3 | 5 | 0 | 1 | 1 | 9 | 0 | 0 |
| Increase of blood vessel | | 2 | 8 | 0 | 0 | 3 | 4 | 2 | 0 | 1 | 8 | 0 | 1 |
| Fragmentation of tunica muscularis mucosae | | 0 | 9 | 1 | 0 | 1 | 6 | 2 | 0 | 1 | 8 | 1 | 0 |
| Fragmentaion of muscularis externa | | 1 | 8 | 1 | 0 | 3 | 3 | 3 | 0 | 1 | 8 | 1 | 0 |

*Degree of histopathological changes; (0) not observed, (1) slightly observed, (2) moderately observed, (3) markedly observed.
Saline, BBG or POCMFr was intramuscularly administered for 4 weeks.

TABLE 2

Experiment II
Gastric Ulcer Healing after 4 Weeks of Treatment

| No. | Saline 0.1 ml/100 g | | | POCMFr 0.1 ml/100 g | | | BBG 0.07 ml/100 g | | |
|---|---|---|---|---|---|---|---|---|---|
|   | a | b | UI | a | b | UI | a | b | UI |
| 1 | 4.6 | 3.0 | 13.8 | 5.3 | 3.4 | 18.0 | 0 | 0 | 0 |
| 2 | 8.7 | 3.2 | 27.8 | 4.8 | 3.9 | 18.7 | 2.6 | 1.2 | 3.1 |
| 3 | 5.0 | 3.0 | 15.0 | 0 | 0 | 0 |   |   |   |
| 4 | 5.2 | 3.8 | 19.8 |   |   |   | 0 | 0 | 0 |
| 5 | 5.8 | 2.8 | 16.2 | 4.6 | 1.3 | 6.0 | 0 | 0 | 0 |
| 6 | 7.1 | 3.2 | 22.7 | 3.2 | 1.1 | 3.5 | 0 | 0 | 0 |
| 7 | 3.3 | 2.0 | 6.6 | 0 | 0 | 0 | 0 | 0 | 0 |
| 8 | 0 | 0 | 0 | 2.8 | 2.3 | 6.4 |   |   |   |
| 9 | 2.2 | 1.3 | 2.9 | 1.0 | 0.5 | 0.5 | 0 | 0 | 0 |
| 10 | 3.0 | 1.2 | 3.6 | 0 | 0 | 0 | 0 | 0 | 0 |
| 11 |   |   |   |   |   |   | 0 | 0 | 0 |
| 12 |   |   |   |   |   |   | 0 | 0 | 0 |
| Mean | 4.0 | 2.4 | 12.8 | 2.4 | 1.4 | 5.9 | 0.3 | 0.1 | 0.3 |
| SE | 0.8 | 0.4 | 2.9 | 0.7 | 0.5 | 2.5 | 0.3 | 0.1 | 0.3 |
| I Saline | | 4.5 ± 0.8 | | | 2.4 ± 0.4 | | | 12.8 ± 2.9 | |
| II CMFr | | 2.4 ± 0.7 | | | 1.4 ± 0.5 | | | 5.9 ± 2.5 | |
| III BBG | | 0.3 ± 0.3 | | | 0.1 ± 0.1 | | | 0.3 ± 0.3 | |

After analysis by unpaired t tests, a = (p 0.05) for

TABLE 2-continued

Experiment II
Gastric Ulcer Healing after 4 Weeks of Treatment

| | Saline 0.1 ml/100 g | | | POCMFr 0.1 ml/100 g | | | BBG 0.07 ml/100 g | | |
|---|---|---|---|---|---|---|---|---|---|
| No. | a | b | UI | a | b | UI | a | b | UI |

POCMFr-treated compared to control (n = 9 and n = 10);
b = (p 0.0002) for BBG vs saline (n = 10 for each)
and c = (p 0.02) for BBG vs CMFr (n = 10 and n = 9).

What is claimed:

1. Method for treating a gastric ulcer comprising administering to a patient with a gastric ulcer an amount of a pharmacological active mixture of bovine brain ganglioside sufficient to heal said ulcer.

2. Method of claim 1, wherein said mixture of gangliosides is administered intramuscularly.

3. Method for treating a gastric ulcer comprising administering to a patient with a gastric ulcer an amount of a pharmacologically active, lipid containing porcine mental extract sufficient to heal said ulcer.

* * * * *

UNITED STATES PATENT AND TRADEMARK OFFICE
CERTIFICATE OF CORRECTION

PATENT NO. : 4,957,741

DATED : September 18, 1990

INVENTOR(S) : Ahmad R. Kamarei et al.

It is certified that error appears in the above-identified patent and that said Letters Patent is hereby corrected as shown below:

<u>TITLE PAGE</u>

In the assignee data:  Add -- Trustees of Boston University, Boston Massachusetts --.

Signed and Sealed this

Twenty-third Day of February, 1993

Attest:

STEPHEN G. KUNIN

*Attesting Officer*   *Acting Commissioner of Patents and Trademarks*